(12) United States Patent
Hein et al.

(10) Patent No.: US 7,302,397 B1
(45) Date of Patent: Nov. 27, 2007

(54) SYSTEM FOR ISSUE IDENTIFICATION, PRIORITIZATION, AND RESOLUTION AND ASSOCIATED METHOD

(75) Inventors: Walter J. Hein, Bothell, WA (US);
Bradley J. Taylor, Everett, WA (US);
Neil S. Smith, Snohomish, WA (US);
Christopher L. Gribskov, Everett, WA (US)

(73) Assignee: The Boeing Company, Seattle, WA (US)

( * ) Notice: Subject to any disclaimer, the term of this patent is extended or adjusted under 35 U.S.C. 154(b) by 200 days.

(21) Appl. No.: 09/656,678

(22) Filed: Sep. 7, 2000

(51) Int. Cl.
*G06Q 99/00* (2006.01)

(52) U.S. Cl. .................. 705/1; 705/2; 705/3; 705/4; 705/5; 705/6; 705/7; 705/8; 705/9; 705/10; 705/80; 700/108; 709/205

(58) Field of Classification Search ............. 705/1–10, 705/80, 51; 709/205
See application file for complete search history.

(56) References Cited

U.S. PATENT DOCUMENTS

| | | | | |
|---|---|---|---|---|
| 5,495,412 A | * | 2/1996 | Thiessen | 705/1 |
| 5,504,890 A | * | 4/1996 | Sanford | 707/3 |
| 5,668,953 A | | 9/1997 | Sloo | |
| 5,671,360 A | * | 9/1997 | Hambrick et al. | 705/9 |
| 5,793,365 A | * | 8/1998 | Tang et al. | 715/758 |
| 5,878,214 A | * | 3/1999 | Gilliam et al. | 709/204 |
| 5,953,707 A | * | 9/1999 | Huang et al. | 705/10 |
| 5,956,491 A | | 9/1999 | Marks | |
| 5,960,173 A | * | 9/1999 | Tang et al. | 709/201 |
| 5,983,074 A | * | 11/1999 | Jansen | 340/7.1 |
| 5,995,951 A | * | 11/1999 | Ferguson | 706/10 |
| 5,999,908 A | * | 12/1999 | Abelow | 705/1 |
| 6,026,148 A | | 2/2000 | Dworkin et al. | |
| 6,177,932 B1 | * | 1/2001 | Galdes et al. | 345/733 |
| 6,222,535 B1 | * | 4/2001 | Hurd, II | 715/733 |
| 6,304,861 B1 | * | 10/2001 | Ferguson | 706/10 |
| 6,571,234 B1 | | 5/2003 | Knight et al. | |
| 6,606,744 B1 | * | 8/2003 | Mikurak | 717/174 |

(Continued)

OTHER PUBLICATIONS

ENIGMA: Engimas wins order from Bombardier Aerospace to web-enable mission-critical maintenance information; Aircraft manufacturer automates dissemination of technical content . . . , Aug. 14, 2000, M2 Communications Ltd., pp. 1-3.*
U.S. Appl. No. 60/173,718, filed on Dec. 30, 1999.*

*Primary Examiner*—Bradley B. Bayat
(74) *Attorney, Agent, or Firm*—Alston & Bird LLP

(57) ABSTRACT

A method of collaboratively identifying, prioritizing, and resolving issues is provided. An issue and/or a comment corresponding to the issue are received over a computer network from a customer and/or an originating entity via respective computer devices and posted on a discussion-capable electronic media accessible to the computer devices, as well as a third computer device. The third computer device is used by a committee comprised of a customer representative and originating entity representative to access the electronic media to separate the posted issues into rejected issues and action issues, at least partially based on the posted comments. The committee prioritizes the action issues and sends resolution directions for each action issue to the customer and/or a manufacturer. Once a resolution proposal for an action issue is received, the committee directs the implementation of the resolution proposal for each action issue before closing the action issue upon completion of the resolution proposal. An associated system is also provided.

18 Claims, 8 Drawing Sheets

U.S. PATENT DOCUMENTS

| | | |
|---|---|---|
| 6,609,100 B2 | 8/2003 | Smith et al. |
| 6,707,469 B1 | 3/2004 | Kelly |
| 2001/0018698 A1 | 8/2001 | Uchino et al. |
| 2001/0018704 A1 | 8/2001 | Kikugawa |
| 2001/0025309 A1 | 9/2001 | Beck et al. |
| 2002/0029187 A1* | 3/2002 | Muller ........................ 705/14 |
| 2002/0184246 A1* | 12/2002 | Shkolnik .................... 707/203 |

* cited by examiner

SYSTEM FOR ISSUE IDENTIFICATION, PRIORITIZATION, AND RESOLUTION AND ASSOCIATED METHOD

FIELD OF THE INVENTION

The present invention relates to management processes and, more particularly, to a system and associated method for collaboratively identifying, prioritizing, and resolving issues.

BACKGROUND OF THE INVENTION

Many industries produce complex systems that have long service lives and thus must be continually monitored and engineered in order to meet, for example, evolving demands of the application as well as safety and maintenance concerns. Such systems may include, for example, aircraft, rail systems, medical systems, weapon systems, certain foods and drugs, and power generation plants where the continued support of the manufacturer and/or other originating entity is not only required for the upkeep of the systems, but possibly also to abide by state, federal, and/or international regulations administered by one or more corresponding agencies or to fulfill the terms of a military contract.

Such a situation is present with, for example, commercial aircraft sold by a manufacturer thereof to an airline which uses the aircraft as a part of its fleet. These aircraft such as, for example, the Models 707, 717, 727, 747, 757, 767, MD-11, MD-80, etc. produced by The Boeing Company are extremely complex and expensive systems that face stringent scrutiny from the Federal Aviation Administration (FAA) in areas related to, for instance, safety and maintenance. However, these aircraft may sometimes experience problems that are neither safety-related nor maintenance-related and thus are not covered by a specific procedure or set of guidelines. Such "non-safety" problems may include, for example, literature pockets experiencing yellowing and/or hazing and broken air diffusers in the lower cargo compartment. These non-safety problems require remedies, nonetheless, particularly when the problem is recurrent.

Typically, when non-safety problems occur in the aircraft, for example, the broken air diffuser, a replacement part is obtained from the manufacturer at a certain cost. If the same part continues to experience failure, a permanent remedy from the manufacturer may be requested. However, such remedies are often requested by a subordinate at a particular airline, rather than by senior management, and such requests may be submitted by the subordinate after varying numbers of incidences. In addition, the problem may not be experienced or regarded as a problem by other airlines. Thus, there is generally no consistent reference as to what constitutes an economic or otherwise significant problem that requires the attention of the manufacturer and the airlines having that model of aircraft in their fleet. Further, when a permanent remedy request is accepted by the manufacturer, the manufacturer often conducts an investigation into the root cause of the problem, rather than just the reported problem itself. Accordingly, a permanent remedy to the reported problem may sometimes encompass a much broader scope to address the root cause as well as associated problems arising therefrom.

Following the action by the manufacturer, the airlines are notified of the remedy through a service bulletin and the remedy is made available at a specified cost, which may include the cost of the investigation and the resources dedicated to determining the remedy. However, the permanent remedy may not be economically justifiable for an airline at the cost cited by the manufacturer. Therefore, an airline may simply choose to ignore the corresponding service bulletin for a variety of reasons and may be justified in doing so since the remedy is not mandated under either safety or maintenance requirements. As such, the permanent remedy may only be implemented by a few airlines having the corresponding aircraft as part of its fleet, if the remedy is implemented at all.

If the recommended remedy is not implemented by the airlines, the manufacturer realizes a loss in the manpower, time, and other resources that were dedicated to resolving the reported problem. In addition and as a consequence, the time required for the manufacturer to address other reported problems may be prolonged, which may lead to dissatisfaction among the airlines as to the responsiveness of the manufacturer. Further, airline dissatisfaction may also result if the manufacturer provides a remedy addressing the root cause of the problem, but which strays too far from directly addressing and which carries a disproportionate cost with respect to the reported problem. In such instances, the manufacturer may be seen as failing to understand the extent of the problem that actually needed to be resolved and the actual concern of the airline regarding the reported problem.

In some instances, individual airlines implement their own remedies for non-safety related problems. In other instances, individual airlines may work with a specific supplier or work within a predefined group such as, for example a "Working Together Team" comprising airline representative and propulsion systems representatives, to resolve a problem. However, the remedies resulting from these processes may be unknown to other airlines experiencing the same problem and may result in unnecessary costs and delays for the manufacturer as well as the other airlines if the problem is addressed anew. In addition, the "problem" reported by an airline may, in actuality, be a request for modification to an existing subsystem for which design and development resources are needed instead of problem-solving capacity.

Such concerns may be experienced by a number of diverse industries, and possibly within a particular industry, where a complex system is involved. Thus there exists a need for a system capable of identifying the customer-reported problems comprising the prevalent concerns of the customers and for which the customers would be most likely to implement a provided remedy. It would also be desirable for the system to be capable of prioritizing the reported problems such that the more urgent issues may be addressed first without unnecessary delay in addressing other less urgent issues. In such instances, it may also be desirable for the scope of the problem, the expected cost of a remedy, and/or the implementation schedule for a remedy to be decided prior to the expending of resources in order to increase the likelihood of customer implementation of the remedy. Further, in determining a resolution to the problem, it would be desirable for the system to be able to account for knowledge of remedies to similar problems developed by other customers and/or remedies to similar problems developed by other customers in conjunction with suppliers and/or vendors. Such a system should also account for a customer's request to implement a modification to the product that requires the allocation of alternate resources of the manufacturer in order to address such a request.

SUMMARY OF THE INVENTION

The above and other needs are met by the present invention which, in one embodiment, provides a method of collaboratively identifying, prioritizing and resolving issues affecting a series administered by an originating entity, more particularly, wherein the series comprises a plurality of similar complex systems and the method is implemented over a computer network through a central site in communication therewith. First, an issue is received at the central site from a first computer device adapted to be used by a customer in possession of a system in the series and/or a second computer device adapted to be used by the originating entity. In such instances, the issue comprises a problem or other concern with the series requiring resolution. In addition, comments corresponding to the issue are then received at the central site from the customer and/or the originating entity in response to the issue. The issue and/or the comments are posted on a discussion-capable electronic media accessible to the first and second computer devices, as well as a third computer device, over the computer network, wherein the electronic media is configured to have a plurality of issues and a plurality of comments posted thereon.

The third computer device further is adapted to be used by a committee comprised of a customer representative and an originating entity representative. The third computer device is also allowed access to the electronic media so as to allow the committee to separate the posted plurality of issues into rejected issues and action issues, at least partially based on the posted plurality of comments. The committee thereafter prioritizes the action issues so as to determine an order in which the action issues are addressed. Further, the committee is allowed to send a set of resolution directions for each action issue, via the third computer device, over the computer network to the customer via the first computer device and/or the originating entity via the second computer device. Following the sending of the set of resolution directions, a resolution proposal is received for each action issue over the computer network, wherein the resolution proposals are accessible by the committee via the third computer device. The committee is then allowed, via the third computer device, to direct the implementation of the resolution proposal for each action issue over the computer network. Following implementation of the resolution proposal, the committee then directs closure of the action issue.

In some instances, the rejected issues may be stored for further monitoring and/or future reference. In addition, the set of resolution directions may further comprise an assignment of the action issue to the customer and/or the originating entity, a suggested cost of the implementation of the resolution proposal, and/or a criteria for designating the action issue as being resolved. Further, in a particular instance, the originating entity may comprise an aircraft manufacture of a series of aircraft, while the issue comprises a non-safety issue.

Another advantageous aspect of the present invention comprises a system for implementing the associated method for issue identification, prioritization, and resolution as described herein. Such a system may be implemented in computer software, or a combination of computer software and hardware, having one or more processing portions for accomplishing an associated method according to other embodiments of the present invention. In a representative embodiment, an electronic bulletin board or other discussion-capable electronic media is initiated and developed on a central computer or computer device that is part of a larger computer network such as, for example, the Internet. Such a central computer or computer device may comprise, for example, a desktop personal computer, a laptop personal computer, a server, a router, a mainframe computer or like devices or combinations thereof capable of implementing the described functions as known to one skilled in the art. Once established on the central computer or computer device, the bulletin board (also referred to herein as a "discussion board") is accessible to a customer through a customer's computer and to an originating entity through an originating entity's computer, with each of the computers being an integral part of the computer network and communicable with the central computer or computer device through, for example, network communication lines.

The discussion board may be used by the customer and/or the originating entity to report problems or other issues requiring resolution, with regard to the complex system produced by the originating entity, so as to obtain a remedy or resolution therefor. In order to list or discuss technical issues regarding the complex system, the customer or the originating entity accesses the discussion board, via the respective computers, over the network communication lines that are in communication with the central computer or computer device. Generally associated with the discussion board on the central computer or computer device are a customer information module and a problem solution board. With this system, the customer and/or the originating entity are able to report and discuss problems with the complex system, wherein the reported problems and corresponding discussion are evaluated by a steering committee via a steering committee's computer in communication with the central computer or computer device through the network communication line.

The steering committee may comprise a customer representative and an originating entity representative, wherein the steering committee monitors the discussion board so as to separate the reported issues into rejected issues and action issues. The action issues are prioritized and further posted on a problem solution board along with resolution directions therefor. The customer and the originating entity may also be in communication with the problem solution board so as to be able to monitor the action issues posted thereon by the steering committee. The steering committee may also post a set of resolution directions for each action issue on the problem solution board. The resolution directions may include, for example, assigning the task of investigating the action issue and producing a resolution proposal to the customer and/or the originating entity. The resolution directions may also include a suggested cost or cost limit for the implementation of a resolution proposal as well as the parameters needing to be fulfilled in order to designate the action issue as being resolved. Upon developing a resolution proposal, the responsible party posts the resolution proposal on the problem solution board via the network communication lines, wherein implementation of the resolution proposal is then directed by the steering committee. Upon completion of the implementation of the resolution proposal, the action issue is directed to be closed by the steering committee.

These elements, alone or in combination, are capable of implementing the associated method of identifying, prioritizing, and resolving issues according to embodiments of the present invention. The customer information module, the discussion board, and the problem solution board are generally implemented in computer software, though the system may also, in some instances, be implemented by a combination of software and hardware, for example, where the system encompasses remote computers, displays, or the like.

Further, the customer information module, the discussion board, and problem solution board may produce databases that are generally stored in, for instance, a memory device incorporated within or otherwise associated with the central computer or computer device. In addition, the central computer may, for example, at least partially include or be disposed in communication with a router, server, switch, or the like for communicating with the customer's computer, the originating entity's computer, and the steering committee's computer, but may also be configured to comprise at least a portion of one of the computers in communication therewith. These elements thus form a system for implementing the associated method according to embodiments of the present invention.

Thus, embodiments of the present invention provide a system capable of identifying customer-reported problems comprising the prevalent concerns of the customers and for which the customers would be most likely to implement a manufacturer-provided remedy. According to embodiments of the invention, the system is also capable of prioritizing the reported problems such that the more urgent issues are addressed first without unnecessary delay in addressing other less urgent issues. Further, the scope of the problem, the expected cost of remedy and/or the implementation schedule for a remedy is decided prior to the expending of resources and thereby increases the likelihood of customer implementation of the remedy. In addition, the system is capable of accounting for knowledge of remedies for similar problems developed by other customers and/or remedies to similar problems developed by customers in conjunction with suppliers and/or venders. Still further, embodiments of the present invention also account for a customer's request to implement a modification to the product that may require the allocation of alternate manufacturer resources in order to address. Thus, a method and system for identifying, prioritizing, and resolving issues according to embodiments of the present invention provides significant advantages as detailed herein.

BRIEF DESCRIPTION OF THE DRAWINGS

Some of the advantages of the present invention having been stated, others will appear as the description proceeds, when considered in conjunction with the accompanying drawings, which are not necessarily drawn to scale, in which.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
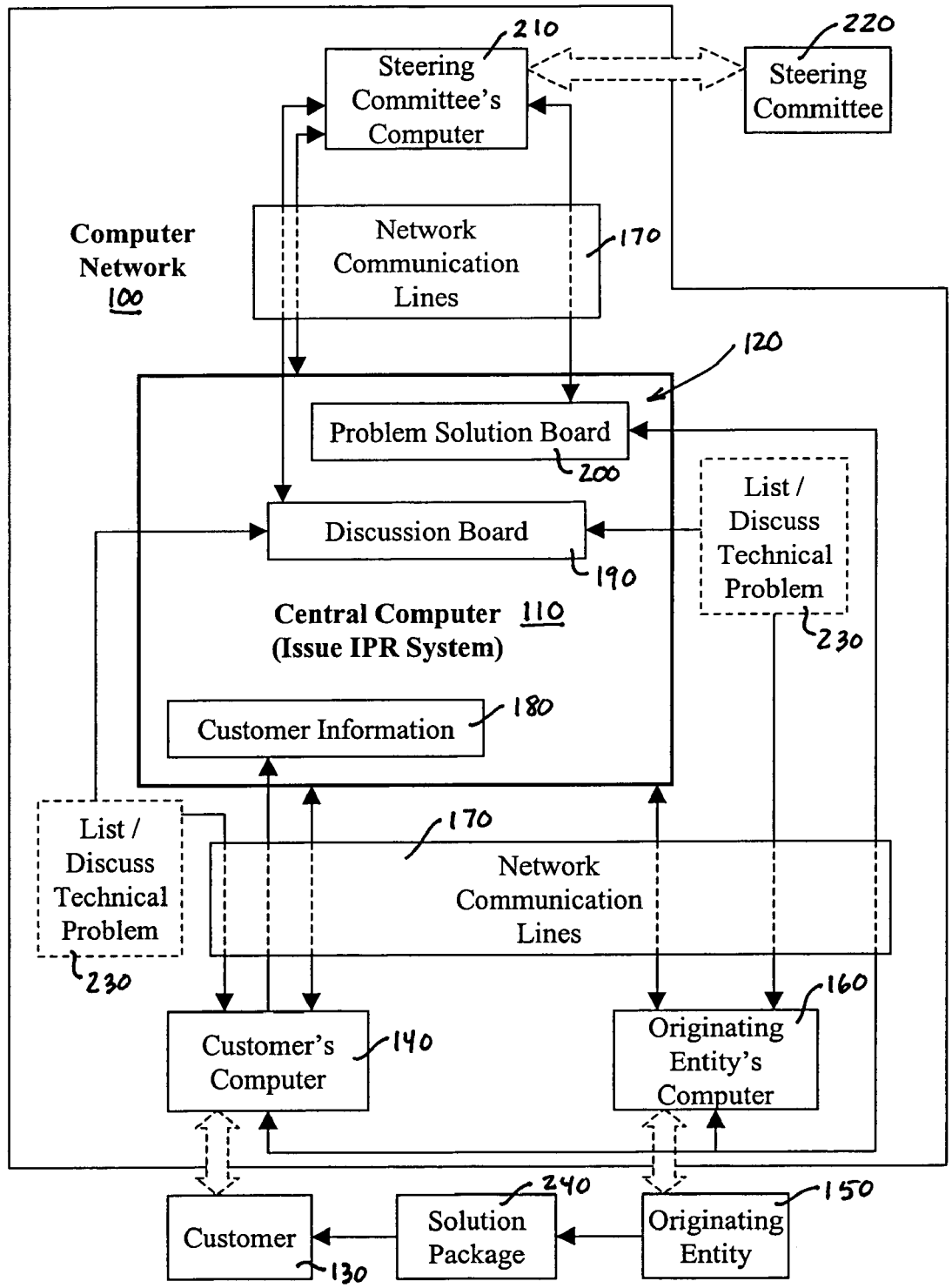
FIG. 1 is a schematic representation of an issue identification, prioritization, and resolution system according to one embodiment of the present invention.

FIG. 1 is a schematic representation of a collaborative system for issue identification, prioritization, and resolution operating over a computer network according to one embodiment of the present invention and is representative of a system capable of implementing a method of identifying, prioritizing, and resolving issues in accordance with further embodiments of the present invention. The issue identification, prioritization, and resolution (IPR) system 120 is initiated and developed on a central computer or other computer device 110 wherein the central computer or other computer device 110 is a part of a larger computer network 100 such as, for example, the Internet. Such a central computer or a computer device 110, referred to herein as "central computer 110" for convenience and brevity, may comprise, for example, a desktop personal computer, a laptop personal computer, a server, a router, a mainframe computer, or like devices or combinations thereof capable of implementing the functions and methods described herein as known to one skilled in the art.

Once established on the central computer 110, the system 120 is accessible to a customer 130 through a customer's computer 140 and to an originating entity 150 through an originating entity's computer 160, each of the computers 140, 160 being an integral part of the computer network 100 and communicable with the central computer 110 through, for example, network communication lines 170. Note that, while a simple schematic of several computers communicable over a computer network is presented herein, it is understood that this concept is representative of communication through an Internet site on, for example, the World Wide Web, and may involve many different computers and associated equipment, wherein the concept of communication via the Internet is known to one skilled in the art. Also note that, in some embodiments, the customer 130 and/or the originating entity 150 may utilize the system 120 in whole or in part, by telephone communication through, for example, an attended or automated call center in accordance with the spirit and scope of the present invention, wherein such a configuration is also known to one skilled in the art.

In order to establish the issue IPR system 120 such as, for example, by establishing one or more issues to be examined so as to publicize the issues affecting the complex systems produced by the originating entity, a customer 130 accesses the central computer 110 via the customer's computer 140 over the network communication lines 170. Generally associated with the system 120 on the central computer 110 are a customer information module 180, a discussion board 190, and problem solution board 200. The customer 130 registers with the customer information module 180 via the network communication lines 170 such that the nature of the customer's holdings of complex systems produced by the originating entity 150 are known, particularly to the originating entity 150. Further associated with the system 120 is a steering committee's computer 210 that is usable by a steering committee 220, wherein the steering committee's computer 210 is communicable with the central computer 110 through network communication lines 170. The outcome of the process administered by the system 120 requires reporting and/or discussion of problems or other issues 230 with respect to the complex system produced by the originating entity 150 and subsequently results in the issuance of a solution package 240 in response to the reported issue from the originating entity 150 to the customer 130.

Note that the customer's computer 140, the originating entity's computer 160, and the steering committee's computer 210 may each generally comprise any computer device or terminal configured to be communicable with the central computer 110 over the computer network 100, wherein, according to the description of the steering committee 220 used herein, a single computer device or terminal may, in some instances, comprise one or more of the computer elements. For example, a single computer device or terminal may comprise both the customer's computer 140 and the steering committee's computer 210 in instances where the customer 130 may be responsible for communications on behalf of the steering committee 220. In other instances, a single computer device or terminal may comprise both the originating entity's computer 160 and the steering committee's computer 210 where the originating entity 150 is responsible for communications on behalf of the steering committee 220.

The issue IPR system 120, including the customer information module 180, the discussion board 190, and the problem solution board 200, is generally implemented in computer software, though the system 120 may also, in some cases, be implemented in a combination of software and hardware. The information gathered through the customer information module 180 is generally stored in, for example, one or more databases in a memory device incorporated within or otherwise associated with the central computer 110. In some instances, for example, elements of the system 120 may include or be disposed in communication with a router, a server, a switch or the like, for appropriately administering the communications between the customer 130, the originating entity 150, and the steering committee 220 as detailed herein. In addition, the discussion board 190 and/or the problem solution board 200 may comprise, for instance, a display or other mechanism for presenting text, graphics, audio, or the like to inform the customer 130 and/or the originating entity 150 of any relevant information pertaining to a reported problem or issue, a corresponding resolution proposal, and/or other information associated with the resolution of an issue through the issue IPR system 120. For example, the discussion board 190 and/or the problem solution board 200 may comprise an electronic bulletin board and/or other discussion-capable electronic media or the like such as, for instance, an "instant message" type system or a "chat board," that is initiated and developed on a central computer or computer device that is part of a larger computer network. Generally, these elements comprise a system, implemented in computer software or a combination of software and hardware, having one or more processing portions capable of executing embodiments of a method for identifying, prioritizing, and resolving issues according to the present invention. Thus, embodiments of such method according to the present invention may be implemented by one or more corresponding processing portions of an associated system, wherein each processing portion may comprise a software component, or both a software and hardware component, capable of implementing one or more of the specified functions. Accordingly, the operation of the issue IPR system 120 and its associated elements may be more particularly illustrated from the description of an associated method corresponding to one embodiment of the present invention.

Figure 2:
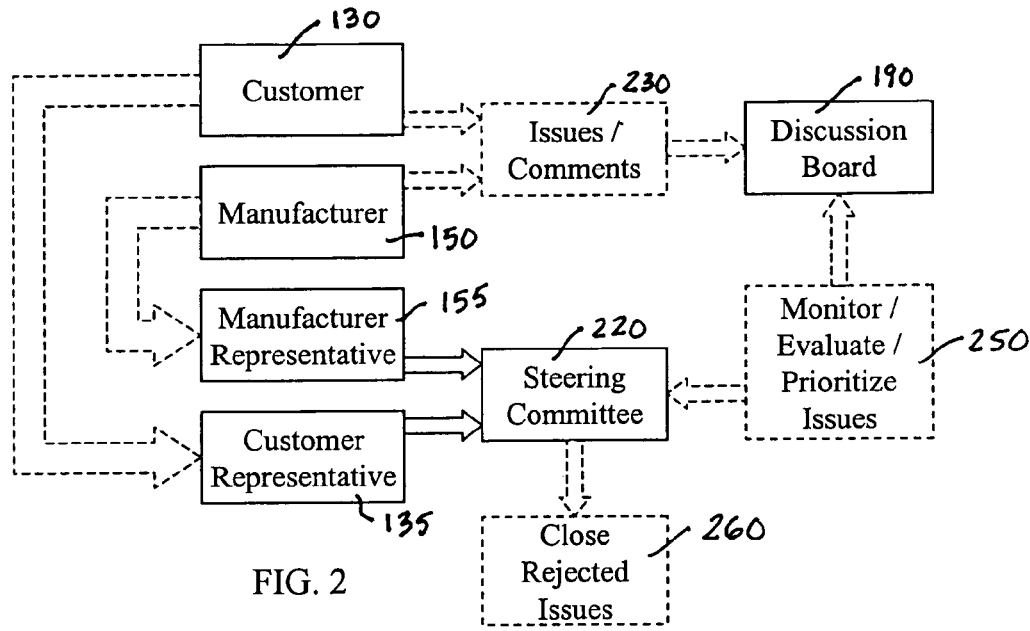
FIG. 2 is a schematic representation of a method of identifying, prioritizing, and resolving issues according to one embodiment of the present invention showing the identification and prioritization of issues.
Figure 3:
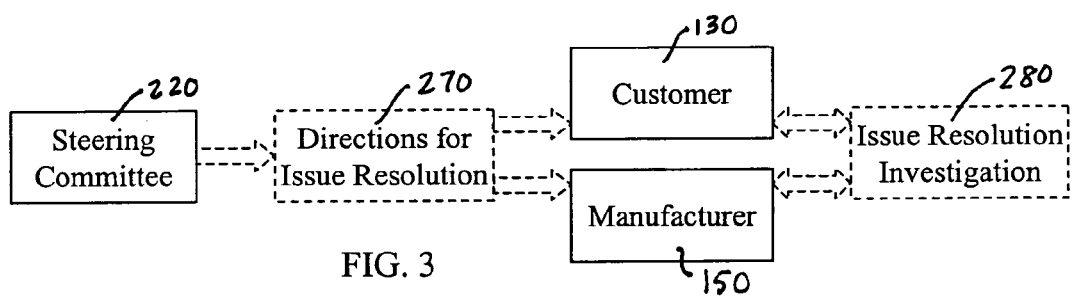
FIG. 3 is a schematic representation of a method of identifying, prioritizing, and resolving issues according to one embodiment of the present invention showing the investigation of identified and prioritized issues.
Figure 4:
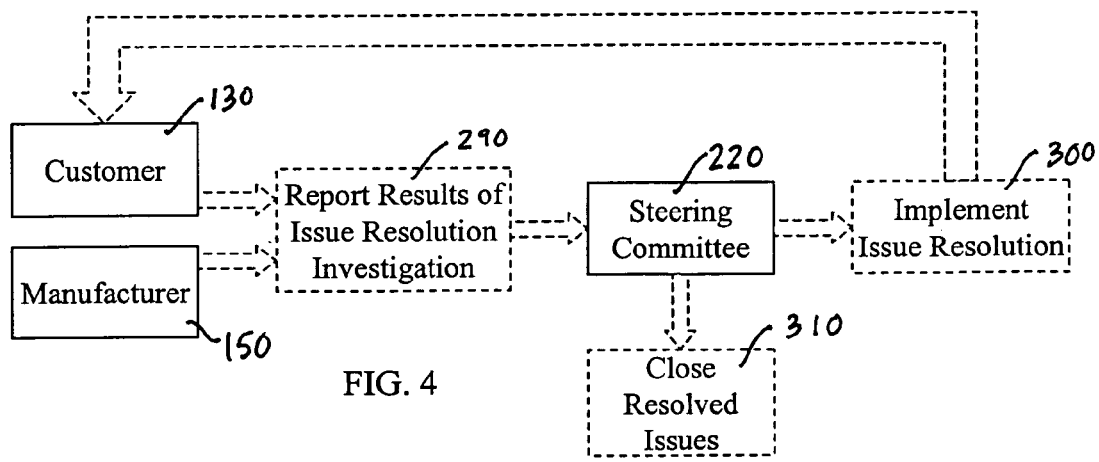
FIG. 4 is a schematic representation of a method of identifying, prioritizing, and resolving issues according to one embodiment of the present invention showing the resolution of identified and prioritized issues.

FIGS. 2, 3, and 4 are schematic representations of a method of identifying, prioritizing, and resolving issues according to one embodiment of the present invention. As detailed herein, the described method may allude to a representative example involving the airline industry where the customer 130 is an airline having a particular aircraft in its fleet and the manufacturer 150 is the manufacturer of that aircraft. However, it would be understood that the present invention is not limited to aircraft, but may include and be applicable to a variety of industries such as, for example, military systems, railroads, power generation systems, or to organizations such as the military and business corporations, wherein a diversed customer base is able to benefit from customer consensus on issues of particular importance as well as from a forum for various customers to discuss and resolve issues. Note that the present invention may also be applicable within a particular organization where the "customer" may be a particular subgroup of the organization and the "manufacturer" comprises the administrator of the subgroups within the organization. Thus, the examples presented herein are not intended to limit the applicability of the embodiments of the present invention, but to illustrate possible applications consistent with the spirit and scope of the present invention.

As shown in FIG. 2, a manufacturer 150 producing a complex system and a customer 130 in possession of the complex system are able to raise issues and/or discuss the same 230 on an electronic discussion board 190 established as part of an issue IPR system 120 on a central computer 110 within a computer network 100. Note that the customer 130 may, in actuality, comprise a plurality of customers, wherein, for example, a customer may represent an airline within a plurality of airlines utilizing a manufacturer's aircraft within its fleet. Accordingly, the issues which may be posted and discussed on the description board 190 may be items determined to have a significant impact to the fleet of a particular airline or an item identified by the manufacturer as having a significant impact on the overall fleet of a particular model of aircraft as determined by the manufacturer's access to similar aircraft across many different airlines. The determined impact may include, for example, the relative impact on the customer with respect to all subsystems affected by the issue as well as the straight economic impact to the customer. Once an issue is posted on the discussion board 190, all customers may review the posted issues to assess the impact of each issue upon their fleet. In addition, the customer 130 and/or the manufacturer 150 posting issues as well as providing comments on the same, may also provide an assessment of the relative level of impact upon the fleet. Further, should a customer 130 and/or the manufacturer 150 have previously encountered the reported issue, details of the resolution of the issue may be provided so as to be accessible to others. The system 120 may also be configured such that questions or other discussion may be exchanged between the customer 130 and the manufacturer 150 integrally with or independent of the discussion board 190.

As further shown in FIG. 2, to facilitate administration of the system 120, the manufacturer 150 appoints a manufacturer representative 155 and the customer 130 appoints a customer representative 135 to a steering committee 220. Thus, the steering committee 220 may comprise a manufacturer representative 155 and one or more customer representatives 135. In some instances, particularly within the aircraft industry, the manufacturer representative 155 may comprise, for example, the fleet support chief in charge of a particular model of aircraft. Within the steering committee 220, a chairperson or co-chairpersons may be appointed, wherein the chair position comprises at least the manufacturer representative and, in some instances, may also comprise a customer representative 135. The chairperson or co-chairpersons generally administer the functions of the steering committee and the duties thereof will be described herein in conjunction with the functions of the steering committee 220, though it will be understood that the functions of the chairperson or co-chairpersons may be described differently in an administrative capacity from the general functions of the steering committee 220.

Generally, the steering committee 220 monitors, evaluates, and prioritizes issues 250 posted on the discussion board 190 where, for example, the postings may be monitored for completeness, adherence to form, and understandability. In addition, the steering committee 220 may solicit comments from individual customers, implement discussion to determine the issues requiring action and the relative priority thereof, implement discussion as to a projected cost of remedy and an appropriate schedule for implementing that remedy, and administer the status of each issue posted on the discussion board 190. For example, the issues that are not eventually deemed an action issue may be rejected and deleted from the discussion board 190. However, in some instances, the rejected issues may be retained for further monitoring and/or as future reference. Issues not meeting the previous criteria for retention in some form are considered rejected issues that are closed 260 by the steering committee 220 and not further considered.

As shown in FIG. 3, once the steering committee 220 administers the selection process for action issues, the steering committee 220 may further discuss the action issues with the customer 130 and/or the manufacturer 150 in order to obtain confirmation of the issues selected for action. Further, the steering committee 220 may consider input from the customer 130 and/or the manufacturer 150 as to the appropriate party to be assigned to investigate a remedy to the reported issue. More particularly, the action issue may be assigned to the customer 130 and/or the manufacturer 150 for the respective party to pursue a remedy therefor. The steering committee 220 may further discuss with the customer 130 and/or the manufacturer 150 the criteria under which the action issue is to be deemed closed where, for example, a reported issue may not be closed until a full implementation of a remedy is obtained or until the responsible party has produced a report or study providing disposition of the reported issue.

Once the discussion amongst the steering committee 220, the customer 130, and the manufacturer 150 is completed, the steering committee 220 may provide a number of administrative functions which may include, for example, assessing the final choices of action issues, prioritizing those action issues, and determining whether the customer 130 and/or the manufacturer 150 is the appropriate party to perform a resolution investigation. The steering committee 220 may also determine a projected cost or cost limit for the implementation of a remedy along with an action schedule over which the investigation and implementation of a remedy is to take place. After determining the closure criteria for the action issue, the steering committee obtains a commitment from the customer 130 to incorporate the remedy under the projected conditions, including such parameters as cost, time, and closure criteria.

As further shown in FIG. 3, once the steering committee 220 completes the necessary administrative tasks for each action issue, the guidelines or directions for issue resolution 270 are forwarded to the customer 130 and/or the manufacturer 150, depending upon the determination of issue ownership by the steering committee 220. The appropriate party then initiates an issue resolution investigation 280 according to the provided guidelines. In the airline industry, for example, an action issue assigned to the customer 130 may be resolved in various ways. For instance, under a "Best Practices" approach, the airlines may discuss, among themselves, prior occurrences of the same or similar problem reported in the action issue and the steps previously taken to resolve the situation. Thus, a customer-based remedy may be provided. Further, the customer 130 may directly contact the supplier of "buyer furnished equipment" (BFE) comprising the particular subsystem reported as being a problem in the action issue, to work therewith to determine a remedy to the issue. In some instances, particularly with engines/propulsion systems which are generally provided by an outside vendor, the airlines may use "Working Together Teams" to assimilate the aircraft with the propulsion system. In these instances, the customer 130 may utilize the Working Together Teams to resolve the action issue.

If the action issue is assigned to the manufacturer 150, however, the manufacturer 150 may implement an internal problem-solving process along the guidelines provided by the steering committee 220 to conduct the appropriate investigation for the action issue. In such instances, the manufacturer 150 may require communication with the customer 130 for additional information, to validate a proposed remedy, and/or to request the customer 130 to provide access to an aircraft to support the testing of any proposed remedy by the manufacturer 150. In other instances, the action issue may be a request from an airline for a modification to an existing subsystem, rather than a problem requiring a remedy. In these instances, the manufacturer 150 may have a dedicated department for addressing such concerns and, thus, an action issue involving a modification to a specific subsystem may be assigned thereto.

As shown in FIG. 4, once the customer 130 and/or the manufacturer 150 completes the issue resolution investigation 280, the responsible party reports the results of the issue resolution investigation 290 to the steering committee 220. The report may include, for example, a proposed remedy for the action issue, an implementation proposal and time frame, and/or an assessment regarding closure of the issue. The steering committee 220 then may direct the implementation of the remedy for the action issue 300 via a service bulletin, the computer network 100, or other agreed method of directing implementation with regard to the customer 130. If consensus as to the closure of the action issue is reached, the steering committee then deems the issue resolved and closes the action issue 310.

Figure 5:
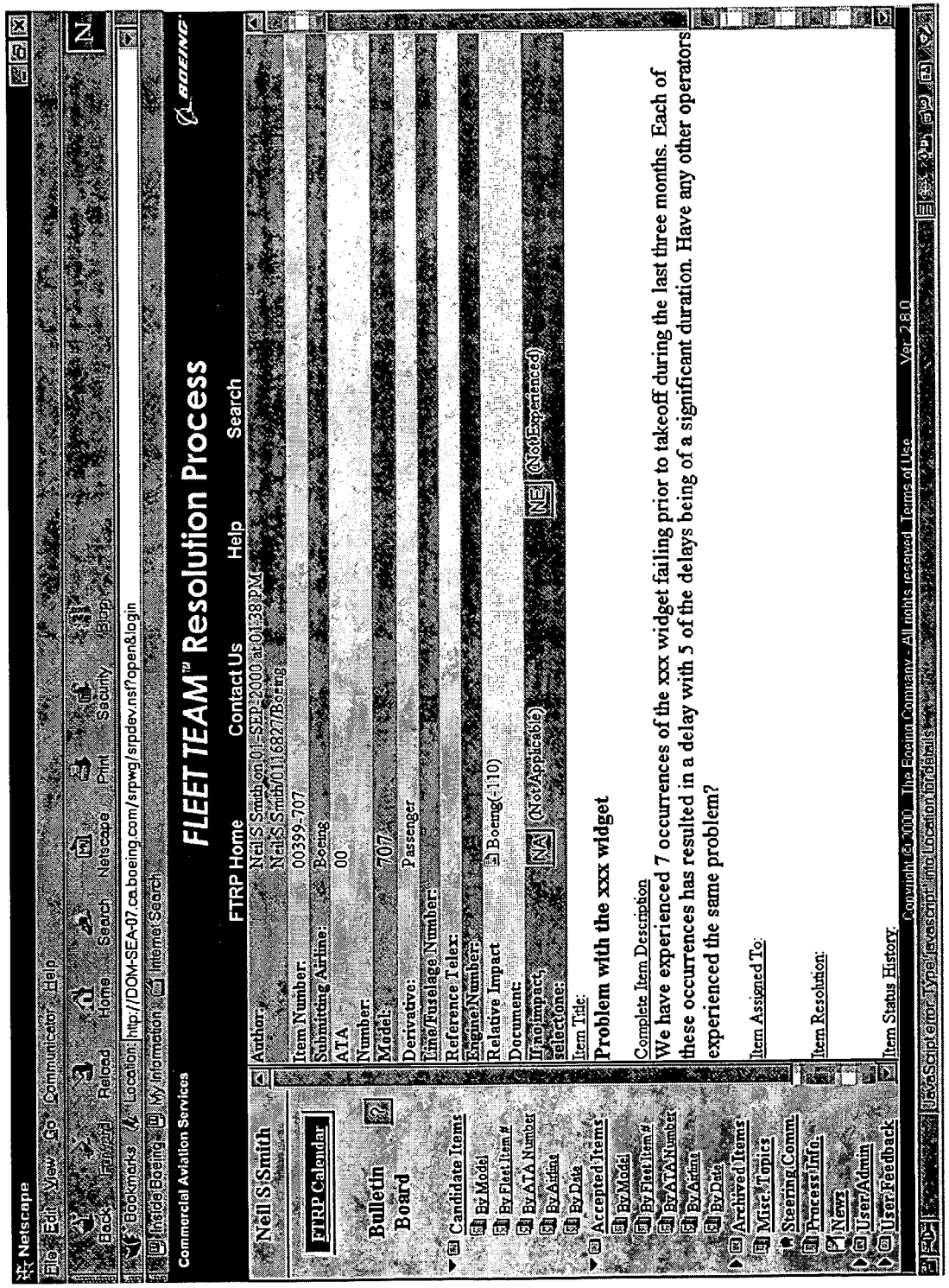
FIGS. 5-10 are schematic representations of an Internet-implemented example of an issue identification, prioritization, and resolution system according to one embodiment of the present invention
Figure 6:
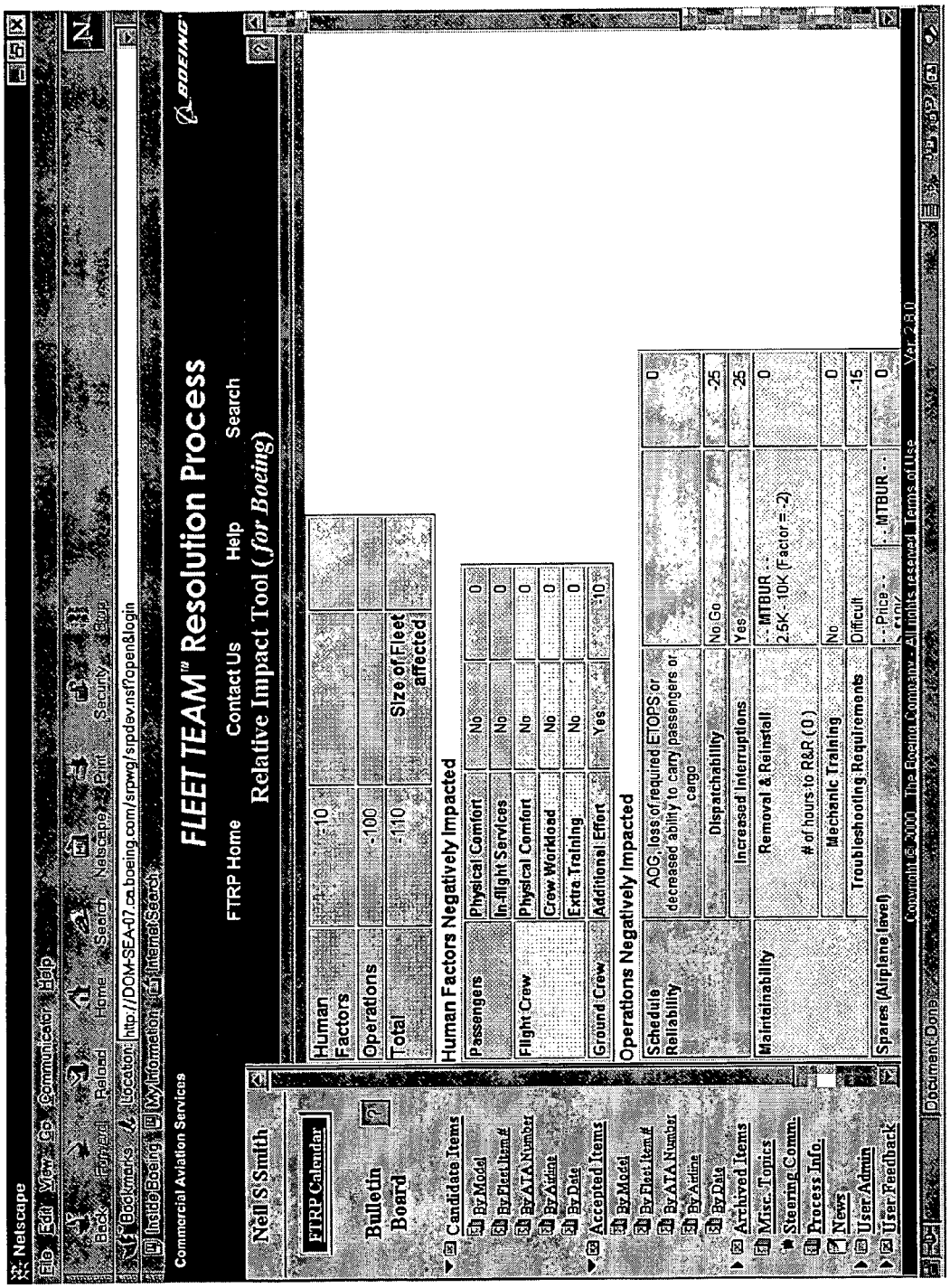
Figure 7:
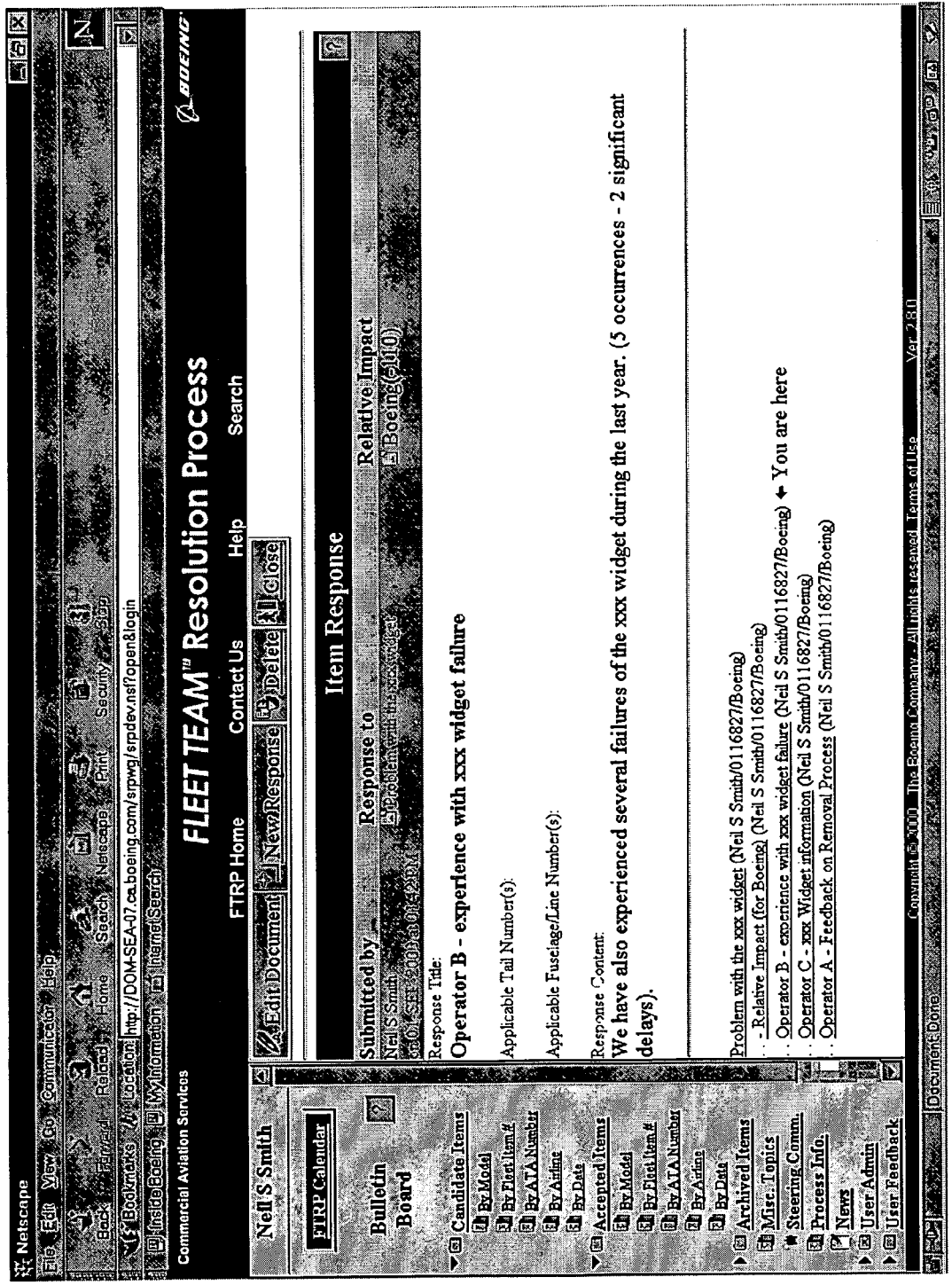
Figure 8:
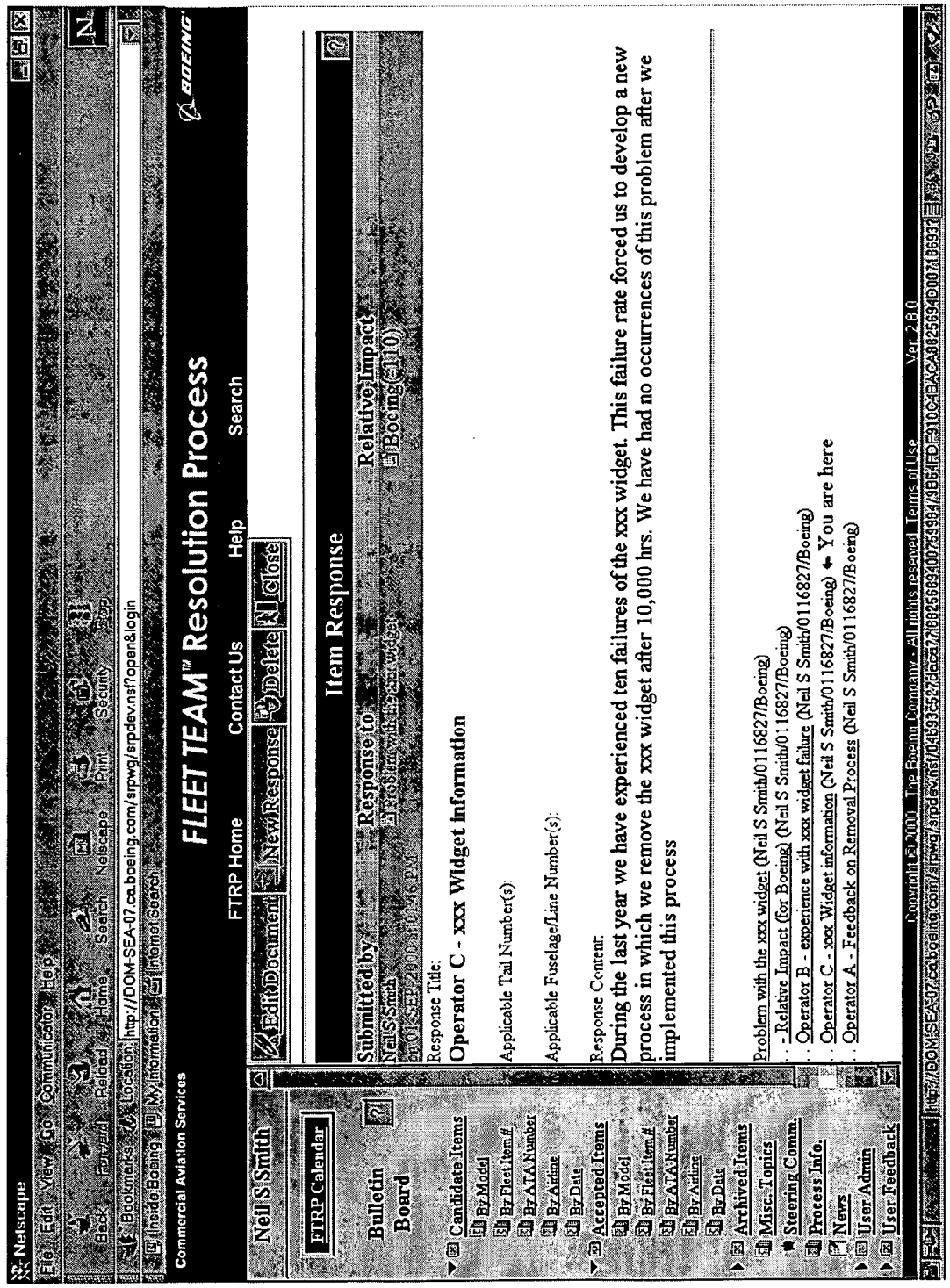
Figure 9:
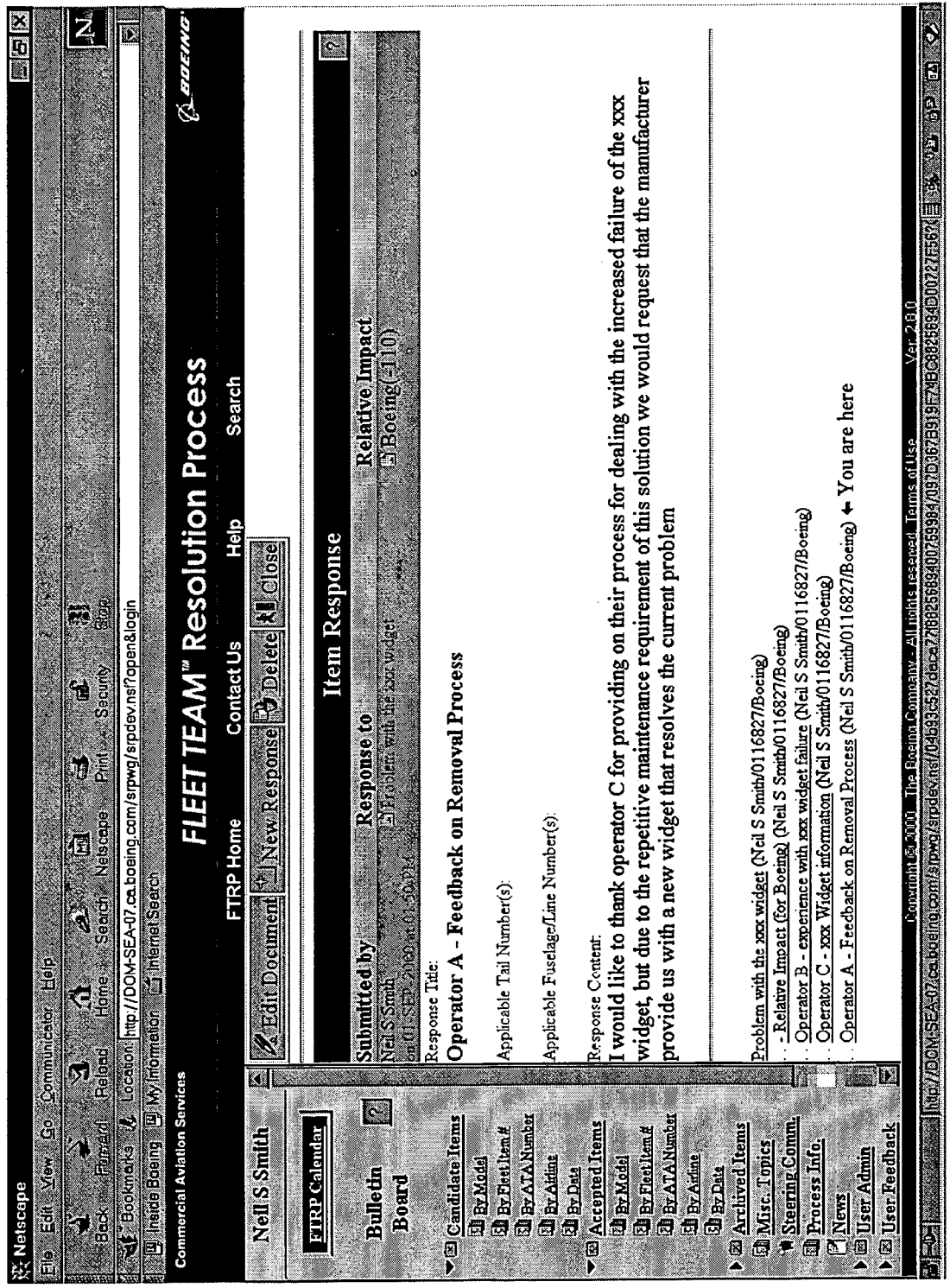
Figure 10:
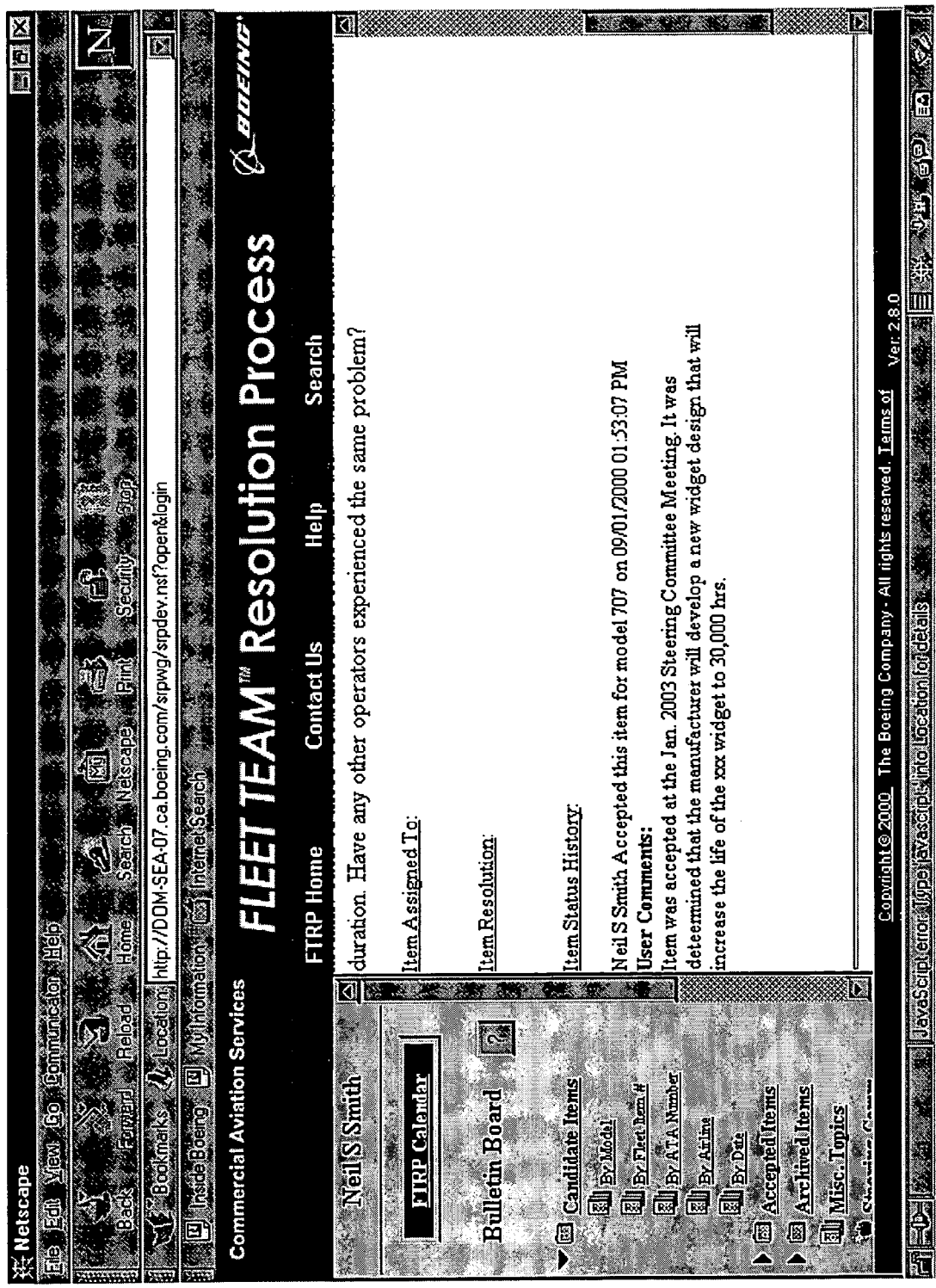

FIGS. 5-10 illustrate an Internet-implemented example of an issue identification, prioritization, and resolution system according to one embodiment of the present invention. FIG. 5 illustrates a posting of an issue received from a customer on the discussion board, wherein the customer also assesses the relative impact of the issue as shown in FIG. 6. In response to the posting of the issue, the customer may receive one or more responses from the originating entity and/or other customers on the discussion board. FIG. 7 illustrates an example of a response detailing another customer's experience with the same issue and the relative impact thereof, while FIG. 8 illustrates still another customer's experience with the same issue and the customer-implemented procedure to resolve the issue. FIG. 9 illustrates the posting customer's assessment of the relevant discussion on the discussion board as well as the request for a permanent solution to the issue. FIG. 10 further illustrates the evaluation and response of the steering committee to the request from the posting customer, wherein the steering committee assigns ownership of the issue to the originating entity and details the relevant parameters affecting the solution. It will be understood, however, that the examples presented herein are for the purposes of illustration and that actual issues may vary considerably in, for example, extent of discussion, complexity of relative impact evaluation, and issue resolution parameters in accordance with the spirit and scope of the present invention.

Thus, embodiments of an issue identification, prioritization, and resolution system according to the present invention provide an improved system for issue resolution, wherein the customer and the originating entity cooperate to agree on actionable issues, the priority of these issues, and the appropriate party and time frame in which a remedy for the action issue is to be provided. In this manner, the customers are capable of providing input into the time frame and the cost of a remedy, as well as input into the operating realities of their business. Such a concept is applicable to a wide variety of systems, particularly where a complex system is involved, and increases the likelihood of customer implementation of the resulting remedy since consensus among the parties is obtained prior to implementing an investigation for a remedy. Embodiments of the system further provide an issue resolution process capable of drawing on resources available to the customer as well as the manufacturer and enables enhanced communication therebetween due to implementation over a computer network accessible by remote computer devises. Further, embodiments of the system are capable of generating cost savings for both parties since time, manpower, and other resources are not wasted on issues which do not present a significant problem for the customer. In addition, the customer may also be able to realize other cost savings since the scope of the remedy and the cost thereof may be discussed and determined before resources are expended for an issue resolution investigation. Embodiments of such a system are also beneficial to the manufacturer in that the customers provide a commitment to implement the remedy prior to the addressing of the action issue. Further, the enhanced communication between the manufacturer and the customers resulting from a system according to embodiments of the present invention may facilitate improved relations therebetween and, thus, may provide a non-tangible benefit to both parties. Thus, embodiments of the present invention provide distinct advantages in the identifying, prioritizing, and resolving of issues than is known in the art.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of collaboratively identifying, prioritizing, and resolving issues affecting a series of similar complex systems, the method being implemented over a computer network and comprising:

assessing an impact of each of one or more issues affecting one or more systems in the series, the assessed impact of each issue having a quantitative value and including a combination of impacted human factors and impacted operations factors, wherein assessing an impact comprises assessing an impact including a combination of impacted human factors and impacted operations factors that each have an associated quantitative value, the value of the assessed impact being the sum of the values of the factors;

receiving the issues for posting on a discussion-capable electronic media, the issues being received by a manufacturer of, or one of a plurality of customers in possession of, the affected one or more systems;

receiving comments corresponding to the posted issues for posting on the electronic media after the respective posted issues, wherein for each issue, the issue and comments corresponding thereto are received by a manufacturer and one or more of a plurality of customers in possession of the affected one or more systems, or by a plurality of the customers, for collaboration with respect to the issue, and wherein one or more of the issues or comments corresponding to one or more of the issues includes the assessed impact of the respective one or more issues;

accessing the electronic media by a committee including representatives of the manufacturer and one or more of the customers, the electronic media being accessed for the committee to identify action issues from the posted issues at least partially based on the posted comments corresponding thereto, and for the committee to thereafter prioritize the action issues, the committee identifying and prioritizing the action issues at least partially based on the assessed impact of the respective one or more issues;

assigning an action issue by the committee to the manufacturer or one or more of the customers for conducting a resolution investigation thereon;

receiving a resolution proposal for the assigned action issue resulting from the corresponding resolution investigation, the resolution proposal being accessible by the committee to evaluate the resolution proposal; and directing implementation of the resolution proposal for the evaluated action issue by the committee, directing implementation including the committee directing closure of the action issue upon completion of implementation of the resolution proposal, wherein the assigning an action issue, receiving a resolution proposal and directing implementation of the resolution proposal steps occur for each of a plurality of action issues at least partially based upon the priority determined by the committee.

2. A method according to claim 1 wherein accessing the electronic media further includes identifying one or more rejected issues from the posted issues, and wherein the method further comprises storing the rejected issues for at least one of further monitoring or future reference.

3. A method according to claim 1 wherein the assigning step further includes sending a set of resolution directions for conducting the respective resolution investigation, the directions including at least one of a suggested cost for resolving the issue, or a criteria for designating the action issue as being resolved.

4. A method according to claim 1 wherein the receiving an issue step comprises receiving a non-safety issue.

5. A system for collaboratively identifying, prioritizing, and resolving issues affecting a series of similar complex systems, the system being implemented over a computer network and comprising:
  a computer device configured to communicate over the computer network with a manufacturer of the series, a plurality of customers in possession of systems in the series, and a committee including representatives of the manufacturer and one or more of the customers, wherein the computer device comprises:
    a first processing portion configured for receiving an assessment of an impact of each of one or more issues affecting one or more systems in the series, the assessed impact of each issue having a quantitative value and including a combination of impacted human factors and impacted operations factors, wherein the first processing portion is configured for receiving an assessment of an impact including a combination of impacted human factors and impacted operations factors that each have an associated quantitative value, the value of the assessed impact being the sum of the values of the factors;
    a second processing portion for receiving the issues for posting on a discussion-capable electronic media, wherein the second processing portion is also configured for receiving comments corresponding to the posted issues for posting on the electronic media after the respective posted issues, wherein for each issue, the issue and comments corresponding thereto are received by the manufacturer and one or more customers, or by a plurality of customers, for collaboration with respect to the issue, and wherein one or more of the issues or comments corresponding to one or more of the issues includes the assessed impact of the respective one or more issues;
    a third processing portion configured for the committee to access the electronic media, identify action issues from the posted issues at least partially based on the posted comments corresponding thereto, and thereafter prioritize the action issues, the committee identifying and prioritizing the action issues at least partially based on the assessed impact of the respective one or more issues;
    a fourth processing portion configured for the committee to assign an action issue to the manufacturer or one or more of the customers for conducting a resolution investigation thereon;
    a fifth processing portion configured for receiving a resolution proposal for the action issue resulting from the corresponding resolution investigation, the resolution proposal being accessible by the committee to evaluate the resolution proposal; and
    a sixth processing portion configured for the committee to direct implementation of the resolution proposal, and direct closure of the action issue upon completion of implementation of the resolution proposal,
    wherein the fourth, fifth and sixth processing portions are configured for each of a plurality of action issues based upon the priority determined by the committee.

6. A system according to claim 5 wherein the second processing portion is further configured for the committee to identify one or more rejected issues from the posted issues, and configured to store the rejected issues for at least one of further monitoring or future reference.

7. A system according to claim 5 wherein the fourth processing portion is further configured to send a set of resolution directions for conducting the respective resolution investigation, the directions including at least one of a suggested cost for resolving the issue, or a criteria for designating the action issue as being resolved.

8. A system according to claim 5 wherein the issues comprise non-safety issues.

9. A system according to claim 5 wherein the manufacturer comprises a manufacturer of a series of aircraft.

10. A method of collaboratively identifying, prioritizing, and resolving issues affecting a series of similar complex systems, the method being implemented over a computer network and comprising:
  assessing an impact of each of one or more issues affecting one or more systems in the series, the assessed impact of each issue having a quantitative value and including a combination of impacted human factors and impacted operations factors, wherein assessing an impact comprises assessing an impact including a combination of impacted human factors and impacted operations factors that each have an associated quantitative value, the value of the assessed impact being the sum of the values of the factors;
  accessing a discussion-capable electronic media including, posted thereon, the issues and comments corresponding to the issues, wherein for each issue, the issue and comments corresponding thereto has been received for posting by a manufacturer and one or more of a plurality of customers in possession of the affected one or more systems, or by a plurality of the customers, for collaboration with respect to the issue, and wherein one or more of the issues or comments corresponding to one or more of the issues includes the assessed impact of the respective one or more issues;
  identifying action issues from the posted issues at least partially based on the posted comments corresponding thereto;
  prioritizing the action issues, wherein identifying and prioritizing the action issues comprise identifying and prioritizing the action issues at least partially based on the assessed impact of the respective one or more issues;
  assigning an action issue to an assignee comprising the manufacturer or one or more of the customers, the assignee being responsible for developing a resolution proposal for resolving the respective action issue;
  sending the action issue and an associated set of resolution directions to the assignee, the set of resolution directions including issue-closure criteria to be met by the resolution proposal for the action issue;
  receiving a resolution proposal for the action issue from the assignee;
  evaluating the resolution proposal for the action issue with respect to the issue-closure criteria; and
  directing implementation of the resolution proposal for the evaluated action issue, including directing closure of the action issue upon completion of implementation of the resolution proposal,
  wherein the assigning, receiving, and directing steps occur for each of a plurality of action issues at least partially based upon the priority of the action issues, and wherein the accessing, separating, prioritizing, assigning, sending, receiving, evaluating and directing steps are performed by a committee including representatives of the manufacturer and one or more of the customers.

11. A method according to claim 10 wherein identifying action issues further includes identifying one or more rejected issues from the posted issues, and wherein the method further comprises storing the rejected issues for at least one of further monitoring or future reference.

12. A method according to claim 10 wherein assigning the action issue comprises assigning the action issue to an assignee according to the priority determined by the committee.

13. A method according to claim 10 wherein sending the action comprises sending the action issue with an associated set of resolution directions including at least one of an implementation cost or an implementation deadline to be met by the resolution proposal for the respective action issue.

14. A method according to claim 10 wherein the manufacturer comprises a manufacturer of a series of aircraft, and wherein receiving an issue comprises receiving a non-safety issue.

15. A method according to claim 10 further comprising requesting, by the committee, approval of the at least one issue-closure criteria associated with the action issue, from at least the customer, prior to assigning the action issue to the assignee.

16. A method according to claim 10 further comprising obtaining, by the committee, a commitment from at least the customer to implement a resolution proposal to the action issue meeting the at least one issue-closure criteria, prior to assigning the action issue to the assignee.

17. A method according to claim 10 further comprising directing implementation of the resolution proposal meeting the associated issue-closure criteria; and closing the action issue upon completion of implementation of the respective resolution proposal, wherein the directing and closing steps are also performed by the committee, and wherein the assigning, sending, receiving, evaluating, directing and closing steps occur for each of a plurality of action issues at least partially based upon the priority determined by the committee.

18. A method according to claim 10 wherein the manufacturer comprises a manufacturer of a series of aircraft, and wherein sending the action issue comprises sending the action issue with an associated set of resolution directions including an implementation cost.

* * * * *